United States Patent [19]

Maggio

[11] Patent Number: 4,828,981
[45] Date of Patent: May 9, 1989

[54] **IMMUNOASSAYS FOR DETERMINING *DIROFILARIA IMMITIS* INFECTION USING ANTIIDIOTYPE MONOCLONAL ANTIBODY REAGENTS**

[75] Inventor: Edward T. Maggio, San Diego, Calif.

[73] Assignee: Synbiotics Corporation, San Diego, Calif.

[21] Appl. No.: 525,999

[22] Filed: Aug. 24, 1983

[51] Int. Cl.$^4$ ............................................. G01N 33/53
[52] U.S. Cl. ........................................ 435/7; 435/68; 435/172.2; 435/240.27; 435/948; 436/86; 436/518; 436/533; 436/534; 436/540; 436/541; 436/548; 530/387; 530/806; 530/808; 530/809; 935/93; 935/110
[58] Field of Search ............. 435/7, 68, 172.2, 240.27, 435/948, 510; 436/533, 534, 538, 536, 540, 541, 548, 86; 530/387, 806, 808, 809; 935/93, 110

[56] References Cited

U.S. PATENT DOCUMENTS

| | | | |
|---|---|---|---|
| 4,200,690 | 4/1980 | Root et al. | 435/7 |
| 4,322,495 | 3/1982 | Kato | 435/7 |
| 4,471,058 | 9/1984 | Smith et al. | 435/172.2 |
| 4,486,530 | 12/1984 | David et al. | 435/7 |
| 4,536,479 | 8/1985 | Vander-Mallie | 435/28 |

FOREIGN PATENT DOCUMENTS 2001172 1/1979 United Kingdom .................... 435/7

OTHER PUBLICATIONS

Potocnjak et al., Science, vol. 215, pp. 1637–1639, (Mar. 26, 1982).
Legrain et al., European Journal of Immunology, vol. 11, pp. 678–685, (1981).
Nelles et al., Journal of Experimental Medicine, vol. 154, pp. 1752–1763 (Dec. 1981).
Abraham et al., Exp. Parasitol., vol. 65, (1988), pp. 157–167.
The Veterinary Clinics of North America, Grieve, R. B., editor, Parasitic Infections, vol. 17, No. 6, (1987), pp. 1463–1518.

*Primary Examiner*—Robert J. Warden
*Assistant Examiner*—Stephen C. Wieder
*Attorney, Agent, or Firm*—Leydig, Voit & Mayer

[57] ABSTRACT

Competitive immunoassays, which employ idiotypic and antiidiotypic monoclonal antibody reagents, are described. These competitive immunoassays are particularly useful for the detection of low concentrations of analyte for which labeled reference analyte is difficult to obtain in quantity. Antiidiotypic monoclonal antibody reagents serves as a substitute for the labeled reference analyte. The antiidiotypic monoclonal antibody reagent exhibits a congruency of structure with one or more epitopes of the analyte or antigen. The antiidiotypic monoclonal antibody is prepared against an idiotypic monoclonal antibody, which, in turn, was prepared against the antigen or analyte. During the immunoassay, the antiidiotypic monoclonal antibody is allowed to compete with the antigen, whose concentration is being determined, for a limited number of antibody binding sites present on an idiotypic antibody, which was also prepared against the antigen or analyte. The idiotypic antibody may be either monoclonal or polyclonal, depending upon the particular immunoassay. The products of the competitive binding reactions are assessed through the use of a signal-generating label attached to either antibody. By employing standards containing known amounts of analyte, the concentration of analyte in a sample fluid may be determined. Analytes detectable by these competitive immunoassays include antigens or antibodies in aqueous fluids, including body fluids such as serum, urine, and the like. Related applications and modifications are also described.

22 Claims, No Drawings

IMMUNOASSAYS FOR DETERMINING *DIROFILARIA IMMITIS* INFECTION USING ANTIIDIOTYPE MONOCLONAL ANTIBODY REAGENTS

BACKGROUND OF THE INVENTION

The invention relates to competitive immunoassays. More specifically, the invention relates to the use of antiidiotypic monoclonal antibody reagents as a substitute for labeled antigen in competitive immunoassays. The invention also relates to the idiotypic monoclonal antibody from which the antiidiotypic monoclonal antibody reagents are derived and to the competitive immunoassays to which these reagents are applied.

Competitive immunoassays provide a sensitive method for the detection and measurement of antigenic substances. These immunoassays usually employ one or more antigens, antibodies, and immunochemical labels arranged in a variety of configurations. Typically, a competitive immunoassay will utilize a labeled ligand (Ag*), which may be either a labeled hapten or a labeled macromolecular antigen. During the assay, the labeled ligand competes with the corresponding unlabeled antigen or analyte (Ag) from sample for a limited number of antibody binding sites (Ab). A review of many aspects of immunoassays by numerous authors is compiled in *Enzyme Immunoassay*, E. Maggio, Ed. CRC Press, Boca Raton, Fla. (1980).

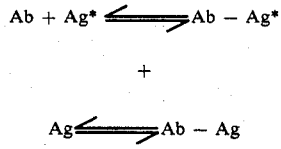

The concentration of antibody binding sites available to bind the labeled ligand is inversely related to the concentration of unlabled ligand (analyte). Measurement of the antibody-bound labeled component, or, alternatively, the unbound labeled component allows the user to relate the signal obtained from the label to the concentration of analyte of interest.

Competitive immunoassays may be either heterogeneous or homogeneous. Heterogeneous immunoassays require a physical separation of the free (unbound) labeled antigen from the antibody-bound labeled antigen. The physical separation of the free and bound labeled antigen enables a measurement of the disposition of the labeled antigen in a competitive immunoassay. Typical labels used in heterogeneous immunoassays include radioactivity, enzyme activity, fluorescence, luminescence, and the like. U.S. Pat. No. 3,709,868 is exemplary of a heterogeneous radioimmunoassay.

Many of the parameters of a suitable separation technique for heterogeneous assays are shared by enzyme, fluorescence, luminescence and radioimmunoassay procedures. In order to maximize precision and sensitivity, one would like to insure complete separation of the free and bound reactions with relatively simple and foolproof manipulations. The separation should be accomplished rapidly, preferably without elaborate or expensive equipment. In addition, an ideal method should be unaffected by the constituents of the sample (serum, plasma, cerebrospinal fluid, urine, saliva, and so forth), be generally applicable to a wide variety of analytes, and be amenable to automation.

The most common methods of separation used for enzyme immunoassay include:
I. Solid-Phase methods
  A. Microtitration plates
  B. Coated tubes or beads
  C. Suspendable microbeads
II. Immunological Precipitation
  A. Second-antibody method The suspendable microbeads and secondary antibody precipitation each require a centrifugation step to effect a physical separation. The centrifugation step is an impediment to automation of the technique. On the other hand, no centrifugation is required when the physical separation is effected by the employment of microtitration plates and coated tubes or beads. The avoidance of a centrifugation step greatly facilitates automation of the assay procedures since the remaining steps of these methods are simple liquid handling steps, i.e., pipetting, diluting, and washing.

Homogeneous immunoassays are used where the binding of antibody to antigen can be shown to directly modulate the signal generated by the label. Homogeneous immunoassays require no separation of the antibody-bound and free labeled components. Typical labels used in homogeneous immunoassays include radionuclides (radioimmunoassays), enzymes (enzyme immunoassays), and fluorophores (fluoroimmunoassays). U.S. Pat. No. 3,817,837 is exemplary of a homogeneous enzyme immunoassay. Less frequently used labels include chemiluminigenic molecules, latex particles, stable free radicals, lytic bacteriophage, tanned red blood cells, gold sol suspensions, and enzyme cofactors or inhibitors. U.S. Pat. No. 4,220,450 is exemplary of a chemiluminescence immunoassay.

The above mentioned assays use polyclonal antibodies and a variety of signal generating labels in various types of immunoassay procedures. U.S. Pat. No. 4,376,110 (David) is exemplary of an immunoassay employing monoclonal antibodies in ways similar to which polyclonal antibodies are used in the above inventions. The David immunoassay employs two idiotypic monoclonal antibodies which compete for antigen In the present invention, an antiidiotypic monoclonal antibody competes with antigen for binding sites on the idiotypic antibody. The present use of monoclonal antiidiotypic antibodies in conjunction with idiotypic antibodies or receptors in immunoassays is an entirely new development in the immunoassay field.

Competitive immunoassays require labeled antigen as a essential component of the reagents, i.e the labeled antigen competes with the unlabeled antigen present in sample for a limited number of antibody binding sites. While many antigens may be inexpensive and readily available, other antigens of interest are difficult to obtain or are expensive. Human antigen purified from vital body tissues (e.g., human heart, brain, muscle, nerve tissue, and the like) can be difficult to obtain. Other antigens may have a naturally low prevalence of occurrence or may be intrinsically labile and subject to denaturation, or chemically unstable. For example, certain esterase inhibitors used as neurotoxins or insecticides are subject to hydrolysis upon storage in aqueous media.

Prior to the present invention, competitive immunoassay techniques were disfavored for the analysis of difficult to obtain antigens. However, the present invention teaches that the labeled antigen can be replaced with labeled antiidiotypic monoclonal antibodies having a structural congruence with the rare or otherwise intractable antigen. The present invention enables the use of competitive immunoassys as a practical means to detect rare or otherwise intractable antigens.

An important class of antigens of particular relevance to the present invention consists of complex macromolecular and poly-macromolecular material; subcellular components such as microsomes, organelles, chromosomes and the like; viral capsids, viral nucleic acids or nucleoprotein complexes or intact viruses; cell membranes; hormone receptors and other structures which occur naturally in biological systems or which, like microsomes, are artifactually generated from structures which occur naturally in biological systems. In the past it has been difficult to produce labeled reagents in a reproducible manner in order to assay for the presence of such materials because of 1.) the variable composition of preparations of such materials, 2.) the colloidal nature associated with preparing soluble extracts of such materials; and many other similar problems.

The present invention provides for the replacement of these difficult to obtain or impossible to use antigens with antiidiotypic antibodies exhibiting congruence of structure with one or more epitopes of the difficult to use antigens; which antiidiotypic antibodies are soluble, easy to use replacement materials. The use of such antiidiotypic antibodies in assays for complex antigen materials thus affords a heretofore unavailable means of performing a group of immunoassays important to the field of clinical and analytical chemistry.

In developing an immunoassay, there are many considerations. One consideration is the signal response to changes in the concentration of analyte. A second consideration is the ease with which the protocol for the assay may be carried out. A third consideration is the variation in interference from sample to sample. Ease of preparation and purification of reagents, availability of equipment, ease of automation, and interaction with ligands, are additional considerations. The assay configuration determines the allowable user protocol(s), assay performance parameters such as sensitivity, specificity, inter- and intra-assay precision, and the speed with which results may be obtained. In assessing the practical usefulness of any of the new immunoassay methodologies, it is particularly informative to examine the assay configuration employed in the assay.

There is a continuing need for new and accurate techniques which can be adapted for a wide spectrum of different ligands which can be used in specific cases where other methods may not be readily adaptable. The present invention advances the immunoassay field by its use of antiidiotypic monoclonal antibodies in conjunction with idiotypic antibodies or receptors.

Definitions

Antigen—Any substance which binds specifically to an antibody.
Antibodies—Specific binding proteins with multiple defined tertiary and quaternary structure.
Isotypic variations—Structural variations exhibited by antibodies in the so-called constant region of their structure which allows them to be segregated into classes which include the IgG, IgA, IgM, IgD and IgE classes (so called isotypes).
Idiotypic Variations or Idiotypes—Structural differences exhibited by antibodies within a given class in the hypervariable regions of their structure; these idiotypic variations, also called idiotypes, determine the shape and structure of the binding site, and thus determine the specificity of the antibody.
Monoclonal antibody—Antibody molecules arising from a single clone of the antibody-producing cells having the same idiotypic and isotypic structure.
Antiidiotypic Antibodies—Antibodies themselves are antigenic and may themselves serve as immunogens. Antibodies which bind to the hypervariable region of a subject antibody (i.e., Idiotypic region or binding site of the subject antibody) are called antiidiotypic antibodies. Thus the subject antibody's binding site can bind either to its complementary antigen, or to an antiidiotypic antibody. In other words, the hypervariable region of the antiidiotypic antibody is a positive three dimensional structural approximation of the structure of one or more of the antigens' epitopes.
Label—An immunochemical label is a substance which may be attached to an antibody or antigen to facilitate the sensitive detection of antigen or antibody or the degree of association of antigen or antibody. Labels commonly used include enzymes, fluorophores, latex particles, enzyme cofactors, chemiluminigenic compounds and radionuclides. All, except gamma-emitting radionuclides, have been shown to be modulatable to steric, allosteric or energy-transfer processes and thus may serve as indicators of antibody-antigen binding without the need for physically separating bound from unbound components in immunological reactions.
Antiglobulin—An antibody which binds to the constant region of another antibody.

SUMMARY OF THE INVENTION

There are two closely related parts to the invention, viz., 1.) the antiidiotypic monoclonal antibody reagents employed in the competitive immunoassays and 2.) the competitive immunoassays which employ the antiidiotypic monoclonal antibody reagents. The competitive immunoassays are used for detecting the presence or concentration of antigen or analyte. In addition to the antiidiotypic monoclonal antibody reagents, the competitive immunoassays may also employ specially adapted idiotypic antibody reagents and antiglobulin reagents.

The present competitive immunoassays share some similarity with prior competitive immunoassays which required labeled reference antigen or hapten during the competitive reaction. The present competitive immunoassays replace the labeled reference antigen with an antiidiotypic monoclonal antibody reagent which exhibits congruence of structure with one or more epitopes of the antigen. This antiidiotypic monoclonal antibody reagent makes it possible for the first time to perform competitive-type immunoassays in cases where such assays were previously not before possible due to the high cost, lability, or unavailability of antigen, or because the use of infectious antigens in diagnostic reagents posed a potential health risk to manufacturers or users.

Each antiidiotypic monoclonal antibody reagent is produced specifically for use in a particular competitive immunoassay. Firstly, the antigen to be assayed is used to raise a hybridoma which produces an idiotypic monoclonal antibody to that antigen. A quantity of the idiotypic monoclonal antibody is then produced and purified. Secondly, the purified idiotypic monoclonal antibody is used to raise a second hybridoma which produces an antiidiotypic monoclonal antibody. The screening of the second hybridoma for antibodies which bind to the purified idiotypic monoclonal antibody results in an antiidiotypic monoclonal antibody which exhibits structural congruence with at least one epitope of the antigen. The antiidiotypic monoclonal antibody is then produced in quantity and purified. The purified antiidiotypic monoclonal antibody may then be labeled in accordance with the nature of the immunoassay in which it will be used.

The purified antiidiotypic monoclonal antibody may be labeled with an enzyme for use in enzyme immunoassays; with a radionuclide for use in radioimmunoassays; with fluorophores for use in fluoroimmunoassays; etc.

The competitive immunoassays of this invention also require idiotypic antibody reagent which was raised to the antigen to be assayed. In many instances, the idiotypic antibody may be labeled in lieu of the antiidiotypic monoclonal antibody. In other instances both the idiotypic antibody and the antiidiotypic monoclonal antibody should be labeled. In all cases it is preferred that the idiotypic antibody be monoclonal. Idiotypic antibody which is monoclonal has a uniform binding affinity for each ligand. However, idiotypic antibody which is polyclonal may also be used in some immunoassays, e.g. the heterogeneous immunoassay using container-bound antibody as in Example 2, (infra). When idiotypic polyclonal antibody is used, it is usually preferred that the label be attached to the antiidiotypic monoclonal antibody.

There are two types of competitive immunoassays, viz., 1.) homogeneous immunoassays and 2.) heterogenous immunoassays. Both types of immunoassays become more facile when an antiidiotypic monoclonal antibody is employed.

Homogeneous immunoassays require that the antibody be labeled with a modulatable label. In the case of homogeneous competitive immunoassays employing antiidiotypic monoclonal antibody reagent, a modulatable label is one which, when attached to an antibody, displays a measurably different signal depending on the ligand binding state of the antibody. For example, if a label is attached to the antiidiotypic monoclonal antibody, the label is modulatable if its signal is measurably different when disposed within antiidiotypic-idiotypic antibody pairs and when disposed on unbound antibody. On the other hand, if a label is attached to an idiotypic monoclonal antibody, the label is modulatable if its signal is measurably different when disposed within antiidiotypic-idiotypic antibody pairs and when disposed within antigen-antibody pairs. In the case of fluoroimmunoassays, it is best if both the idiotype and the antiidiotype monoclonal antibodies are labeled with fluorophores. It is preferred that the fluorophores should be chosen such that quenching occurs in antiidiotypic-idiotypic antibody pairs but not with antigen-idiotype pairs.

In the case of heterogeneous competitive immunoassays employing antiidiotypic monoclonal antibody reagent, it is required that the antiidiotype-idiotype pairs be physically separable from either the antigen-idiotype or unbound antiidiotype or from both. The preferred methods for physical separation include solid-phase methods and immunological precipitation methods, as discussed in the background section. In the solid-phase methods, either antibody may be attached to the solid-phase carrier and either antibody may be linked to a label. One of the preferred embodiments is a method employing the antiidiotypic monoclonal antibody which is both labeled and attached to a solid-phase carrier. Utilizing this preferred embodiment, either monoclonal or polyclonal idiotypic antibody may be utilized in the the competition reaction. However, there is some preference for the idiotypic monoclonal antibody.

The competitive immunoassay itself has three essential phases, viz., 1.) the competition binding reaction amongst the antigen, the idiotypic antibody reagent, and the antiidiotypic monoclonal antibody reagent, 2.) the detection of the reaction products by the measurement of label disposed in idiotypic-antiidiotypic antibody pairs, and 3.) the determination of the presence or concentration of antigen in a sample by relating the detection of label of antibody pairs to data derived from antigen standards.

A preferred sequence for combining the reactants in the assay mixture is to first combine the antigen and the idiotypic antibody reagent and then to add the antiidiotypic monoclonal antibody reagent. This sequence is preferred if the detection step is to occur prior to a state of equilibrium in the assay mixture. Equilibrium may be slow due to the high binding affinities of the antigen and antibodies or due to the occurrence of irreversible processes. Greater sensitivity may be achieved by measuring a non-equilibrium assay mixture, however, there is a concomitant risk of greater scatter. A second sequence for combining the reactants in the assay mixture is to first combine the antigen and the antiidiotypic monoclonal antibody reagent and then to add the idiotypic antibody reagent. This sequence may sometimes result in less sensitivity than the first sequence, especially if the final assay mixture is not at equilibrium. A sequence, where the two antibodies are first combined and then added to the antigen, should be used only if the the final assay mixture is known to approach equilibrium.

The protocol for detecting the label disposed within antibody pairs in the assay mixture will depend upon the type of label used. Although the antibody reagents of the present immunoassay are novel, the labels are taken from the prior art. The protocols for detecting these labels will be obvious according to the prior art.

In order to determine the presence or concentration of antigen in a sample from the detection of label disposed in antibody pairs, said detection must be compared to data derived from antigen standards. The antigen standards have a known concentration and are processed by steps identical to the assay of the sample fluid. Assay mixtures of the antigen standards are formed and the presence or concentration of label which is disposed within antibody pairs is detected. The concentration of the label is correlated with the known concentration of the antigen standards. The level of detection of label within antibody pairs of the assay mixture for the unknown antigen sample can then be correlated with the antigen standards to indicate the concentration or presence of the antigen in the sample.

The antiidiotypic monoclonal antibody reagent can also be used in an assay of an idiotypic antibody. Antiidiotypic monoclonal antibody is raised to the idiotypic antibody; produced in quantity; purified; and attached to a solid-phase carrier. In order to assay for the idiotypic antibody, the solid-phase carrier with attached antibody is then mixed with the sample. The idiotypic antibody will bind to the solid-phase carrier via the antiidiotypic monoclonal antibody. The solid-phase carrier is then physically separated from the solute. Labeled antiglobulin to the idiotypic antibody is then combined with the solid-phase portion, so as to bind to the idiotypic antibody which is bound to the solid-phase carrier via the antiidiotypic monoclonal antibody. The detection of label is then correlated with standards to determine the presence of idiotypic antibody.

It is a purpose of this invention to provide a substitute reagent for reference antigen in competitive immunoassays, the substitute reagent being antiidiotypic monoclonal antibody reagent.

It is a purpose of this invention to provide protocols for competitive immunoassays which employ antiidiotypic monoclonal antibody reagent as a substitute for reference antigen.

It is a purpose of this invention to provide protocols for competitive immunoassays which are either heterogeneous or homogeneous and which employ antiidiotypic monoclonal antibody reagent as a substitute for reference antigen.

It is a purpose of this invention to provide a substitute reagent for antigen in immunoassays of idiotypic antibody, the substitute reagent being antiidiotypic monoclonal antibody reagent.

It is a purpose of this invention to provide protocols for immunoassays of idiotypic antibody which employ antiidiotypic monoclonal antibody reagent as a substitute for antigen.

DETAILED DESCRIPTION OF INVENTION

Example 1. Antiidiotypic Monoclonal Antibody Reagent may be derived from antiidiotypic monoclonal antibody (Anti-Id) which is prepared against a murine idiotypic monoclonal antibody (Id) which recognizes the parasite Entamoeba Histolytica. The Antiidiotypic Monoclonal Antibody Reagent was prepared as follows:

A. Production of Idiotypic Monoclonal Antibody

Cells from a murine hybridoma cell line which secrete monoclonal antibodies to Entamoeba Histolytica strain HK-9 were grown in tissue culture in DMEM medium containing 10% fetal bovine serum, with a 10% partial pressure of carbon dioxide, and 37 degrees Centigrade. Cells were harvested, washed in serum-free medium, and resuspended in serum-free medium or phosphate buffered saline to yield cell concentration of $6-10\times10(6)$ cells/mL. BALB/c mice were previously primed by interperitoneal injection of 0.5 mL pristane (2,6,10,14-tetramethyl pentadecane). Approximately $3-5\times10(6)$ cells in 0.5 mL were injected into each mouse. After 7-10 days, ascitic fluid which accumulated in the mouse peritoneal cavity was collected with an 18 to 20 gauge, ¼" needle. After centrifugation at 2800 g for 45 minutes, the ascitic fluid was filtered through a 0.45 micrometer filter. The immunoglobulin fraction was precipitated with 50% ammonium sulfate and dialyzed exhaustively against PBS, to yield the idiotypic monoclonal antibody (Id).

B. Production of a Hybridoma secreting Antiidiotypic Monoclonal Antibody

The Id was emulsified with complete Freunds adjuvant and 50 micrograms of the Id in 200 microL of the emulsion were injected into mice. After booster injections of similar composition at 1 week and 3 weeks, the mice were sacrificed, their spleens removed, placed in a 60 mm petri dish containing 4 mL of serum-free medium. A single suspension of splenocytes was generated by teasing the spleen with forceps. The splenocytes were transferred to a 50 mL centrifuge tube and enough medium was added to yield a total volume of 40-45 mL. The splenocytes were centrifuged for 10-15 minutes at 800 g and the pellet was washed by resuspension and centrifugation and brought up in 10 mL media. Murine myeloma cells (cell line P3X63.Ag8.653) were added to a ratio of 1:6 myeloma cells to splenocytes. Polyethlene glycol (PEG) was melted at 56 degrees Centigrade in a water bath and 0.35 mL was added to 0.65 mL media at 37 degrees Centigrade. The PEG solution was mixed and added to the cell mixture in a dropwise fashion to promote fusion of the cells. Then 9 mL of DMEM, 10% FBS was added and the cell mixture washed by centrifugation. Washed cells were placed into 200 mL HAT medium containing $2\times10(6)$ thymocytes/mL. The cell suspension was then dispensed into eight 96 well plates (25 mL/plate). At days 10 and 18, the media from each of the 96 well plates was removed and replaced with fresh media. Wells containing hybridomas were detected by assaying the supernatants for antiidiotypic monoclonal antibody (Anti-Id) by enzyme immunoassay (infra). Hybridoma cells found to secrete useful Anti-Id were expanded in tissue culture. Part of the culture was frozen in liquid nitrogen for storage. Part of the culture was injected into mice for production of ascitic fluid and antibodies. Monoclonal Anti-Id was isolated according to the procedure described above for Id.

C. Production of an Antiidiotypic Monoclonal Antibody Reagent (Anti-Id lysozyme conjugate)

Anti-Id produced by the the hybridoma was purified from murine ascites by precipitation with 50% saturated ammonium sulfate followed by exhaustive dialysis against phosphate buffered saline (PBS).

Lysozyme (from egg-white) was prepared for coupling to the Anti-Id as follows:

Lysozyme is labeled with sulfhydryl groups using S-acetyl-mercaptosuccinic anhydride by the method of Klotz and Heiney (Habeeb, H.F.S.A. (1972) Methods in Enzymology (Hirs. C.H.W., and Timasheff, S.N.,eds.), Vol XXV, p457, Academic Press, New York). Prior to labeling, the S-acetylmercaptosuccinic anhydride is purified by addition of one equivalent of glacial acetic anhydride followed by crystallization from five parts benzene and one part hexane. Sulfydryl groups on the enzyme are titrated with DTNB (5,5'-dithiobis (2-nitrobenzoic acid)), according to the method of Klotz and Heiney, ibid. Just prior to coupling, the thiol group is deblocked by reaction with 0.1M hydroxylamine for 20 minutes at 4 degrees Centigrade in pH 7.5, 50 mM potassium phosphate buffer. The deblocked thiolated enzyme is then passed through a $0.9\times28.5$ cm Sephadex G-25 column which has been equilibrated with 50 mM K2HPO4/KH2PO4, 20 mM EDTA pH 5, saturated with nitrogen. The protein peak is collected in a 3.0 mL volumetric, flushed with nitrogen, sealed and stored at 4 degrees Centigrade. The collected peak is used within 2 hours for the coupling reaction with the maleimide derivatized Anti-Id described below. The chemical yield of the overall labeling and deblocking reactions is typically about 60% as determined by titration of sulfhydryl groups with DTNB.

The purified Anti-Id was prepared for coupling to Lysozyme as follows:

The purified Anti-Id was labeled with the N-hydroxysuccinimide ester of maleimide (NSH maleimide) according to the method of Keller and Rudinger (Keller, 0. and Rudinger, J., Helv. Chimica Acta 58, 531 (1975)). A solution of Anti-Id at 4.0 mg/mL was prepared in potassium phosphate buffer, adjusted using 1N NaOH. An aliquot (200 microL) of solution containing 2.1 mg of NSH maleimide/mL of dry dimethyl formamide was added to the Anti-Id at 4 degrees Centigrade with vigorous stirring. After 30 minutes, the pH of the solution was lowered to 6.5. The mixture was then passed through a 0.9×28.5 cm Sephadex G-25 (medium) column which had been equilibrated with 0.05 M EDTA, saturated with nitrogen. As soon as the protein peak began to elute from the column, it was collected and stored in a sealed flask under nitrogen. Maleimide groups were determined by reaction with excess beta-mercaptoethanol and the titration of excess thiol with dithio dinitro benzoic acid (DTNB). Typically 4–12 maleimide groups are attached to the Anti-Id.

The maleimide labeled Anti-Id was conjugated to the thiolated lysozyme and the conjugate was isolated as follows:

The two proteins are then coupled under nitrogen to prevent oxidation of the sulfhydryl groups. Thiolated lysozyme (2.0 mL) is added to maleimide labeled Anti-Id (1.0 mL) very slowly with stirring in a ratio of 1.8 sulfhydryl groups for each maleimide. The pH is raised to 6.7 and the reaction mixture is stirred for one hour at room temperature, then for 72 hours at 4 degrees Centigrade. Then 0.2 mL of $10^{(-2)}$M beta-mercaptoethanol is added to quench any unreacted maleimides and to prevent cross-linking of the proteins by reaction of maleimide groups with amines. The solution is stirred for 30 minutes at room temperature and the conjugate is purified on a 0.9×58 cm Sephadex G-200 column which has been equilibrated with 0.1M Tris-HCl pH 7.4. The high molecular weight conjugate is separated completely from the unconjugated Anti-Id and lysozyme. The Anti-Id lysozyme conjugate is diluted 1:25 in 0.2M PBS pH 7.4, 1.0 mg/mL BSA. A 0.25 mL aliquot of the dilution in a 1.1 mL assay will yield final concentration of about $1 \times 10^{(-8)}$M conjugate in the assay.

Example 2. A Homogeneous Competitive Immunoassay Employing Antiidiotypic Antibody Reagent (Anti-Id lysozyme conjugate) for the detection of an antigen on the parasite entamoeba Histolytica may include the following steps:

Step 1. 25 microL of Id and 250 microL of buffer (tris-/maleic acid, pH 6.0) are combined.

Step 2. 25 microL of sample or calibrator solution is added to 250 microL of the assay mixture.

Step 3. 25 microL of the Anti-Id lysozyme conjugate solution is added to 250 microL of of the assay mixture.

Step 4. 25 microL of a substrate (micrococcus lysodeikticus cells suspended in buffer) is added to 250 microL of the assay mixture.

Step 5. The assay mixture is vortexed and immediately aspirated into a spectrophotometer equipped with a thermostatted flow cell set at 30 degrees Centigrade, e.g., into a Gilford 300N spectrophotometer. The rate of decrease in optical density (turbidity) at 405 nm is monitored for 120 second after a 30 second delay in which linearity of the assay is established.

Upon addition and binding of Id to the conjugate, the enzymatic activity of the conjugate is found to decrease markedly to a range between 20% and 98%. Upon addition of antigen (Entamoeba histolytica extract or tissue culture supernatant) the extent of inhibition is found to decrease in proportion to the amount of antigen added as such antigen displaces the Anti-Id/Id binding. Thus a standard curve for the homogeneous immunoassay of E. histolytica antigen may be generated.

Because Anti-Id and Id are both immunoglobulins, they exhibit gross structual similarity (isotypic similarity). Furthermore, because the Anti-Id and Id can combine with identical stoichiometry in a ligand-ligand pair, unlike the multiple binding which frequently occurs in polyclonal antibody-antigen interactions, either the Anti-Id or Id may be regarded equivalently as either the binding or receptor ligand. As such, in the present invention either Anti-Id or the Id may be interchangeably labeled with enzyme in generating useful assays.

Example 3. Heterogeneous Immunoassay Employing Antiidiotypic Antibodies:

Murine monoclonal antibodies recognizing a soluble protein purified from Dirofilaria immits are prepared according to a procedure analogous to that described in Example 1. D. immitis antigen is prepared as follows: Dirofilaria immitis (0.42 g), mixed males and females, are homogenized in 25 mL PBS for 2 minutes at 15 degrees Centigrade, and stored overnight at 4 degrees Centigrade. After centrifugation, the supernatant is acidified by addition of 10% trichloroacetic acid (TCA) to pH 3.5 at 15 degrees Centigrade. In some instances, it may be necessary to correct for excessive additions of TCA by addition of 1N NaOH to bring the pH back to 3.5. After centrifugation the soluble protein in the supernatant is centrifuged and dialyzed exhaustively against buffer at 4 degrees Centigrade. Monoclonal idiotypic antibodies (Id) recognizing D. immitis thus generated are isolated from murine ascites by ammonium sulfate precipitation as described in Example 1. Purified antibody is used to immunize BALB/c mice and antiidiotypic antibodies (Anti-Id) are generated according to the procedure described in Example 1.

A heterogeneous immunoassay is constructed as follows:

96 well microtiter plates (Dynatek) are coated with Anti-Id or Id (100–200 ng/well) in sodium borate buffer (50 microL/well) by allowing the Anti-Id or Id to remain in each well for four hours at 37 degrees Centigrade, followed by approximately 14 hours at 4 degrees Centigrade, after which the Anti-Id or Id is removed from the wells by decanting. The wells are washed three times with phosphate buffered saline containing 0.025% tween. The plates are allowed to dry. Anti-Id or Id are coupled to horseradish peroxidase (HRP) according to the method of Nakane (Nakane, P. K., and Kawaio, A. T., Histochem and Cytochem, 22 1084 (1974)). Those slates coated with Anti-Id were found to bind Id-HRP conjugate. Those plates coated with Id were found to bind Anti-Id-HRP conjugate. Binding of either Id-HRP or Anti-Id-HRP is determined by measurement of HRP activity bound to the plate using the assay described below.

To each well is added 150 microL of enzyme conjugate in PBS pH 7.4. If antigen is to be added, it should be added prior to or at the same time as addition of conjugate. The plates are incubated for 30 minutes and then washed with PBS three times by decanting. ABTS (2,2-azino-di-(3-ethylbenzthiazoline) sulfonic acid) 2 g/80 mL water is prepared and stored at 4 degrees Centigrade. Hydrogen peroxide 0.01% is prepared by dilution of 30% peroxide into water. To initiate HRP measurement, 50 microL of ABTS and hydrogen peroxide are added to the wells. Color development depends upon enzyme concentration but is typically observed over 5-30 minutes.

In both cases, i.e., when either anti-Id or Id coated plates are used with their complementary conjugate, the addition of antigen (D. immitis soluble protein) is found to compete with conjugate. Thus increasing amounts of antigen results in decreased conjugate bound to the plate thus allowing the generation of a standard curve by plotting observed HRP-enzyme activity versus antigen concentration.

The use of polyclonal Id, derived from the serum of animals immunized with D. immitus extract, is found to yield similar results Example 4. Detection of Antibody Using Antiidiotypic Monoclonal Antibody Using the plates coated with Anti-Id described in Example 3, the detection of antibody in serum taken from goats immunized with D. immitis antigen may be accomplished. For example, goat serum from immunized goats serially diluted in phosphate buffered saline is added to the wells of a microtiter plate coated with Anti-Id. The binding of goat antibody is detected with rabbbit anti-goat-IgG conjugated to HPR by the method used in Example 3 and using the standard ABTS assay for HRP also described in Example 3. Increasing dilutions (i.e., lower concentrations) of goat antibody, result in lower HRP enzyme activity bound to the plate.

Example 5. Fluorescence Energy Transfer Immunoassay Using Antiidiotypic Monoclonal Antibodies Idiotypic Antibodies (Id) to E. histolytica and the corresponding antiidiotypic antibody (Anti-Id) as described in Example 1 are labeled with fluorescein isothiocyanate (FITC) or rhodamine isothiocyanate (RITC) according to the following procedure: 10 mg of Id or Anti-Id are dissolved in 1 mL pH 9.0 phospate buffered saline, 0.1M, and 0.1mL of 1 mg/mL of FITC or RITC is added with stirring at room temperature. The pH is adjusted to pH 9.5 with 0.1M tribasic soduim phosphate. Free FITC or RITC is removed from the protein (Id or Anti-Id) by chromatography on an 0.8×8 cm G-25 Sephadex column eluted by pH 7.5 PBS.

Energy transfer immunoassays (for example as described in U.S. Pat. No. 3,996,345) rely upon the quenching of fluorescence observed for a fluorescent dye when that dye is brought into close proximity (e.g., within 50 angstroms) to another dye whose absorbtion maximum at least partly overlaps the emission maximum of the fluorescer. In the present example, this occurs when an RITC-labeled Id (RITC-Id) binds to an FITC-labeled Anti-Id (FITC-Anti-Id). Addition of E. histolytica antigen blocks binding of labeled Id to labeled anti-Id, thus preventing the quenching of fluorescence.

To a series of 1 cm disposable square cuvettes suitable for fluorescence determinations (e.g., Evergreen) is added 1 mL 0.05M phosphate buffer, pH 8.2 containing 0.5 mg/mL BSA. FITC-Anti-Id 100 microL, (0.05 mg/mL) is added to each cuvette. Increasing amounts of RITC-Id are added and fluorescence measured at 480 mm excitation, 520 mm emission using a spectrofluorimeter. Quenching of fluorescence is significant with decreases in excess of 30%. Significant quenching is observed at 150 microL RITC-Id, 0.05 mg/mL.

A second set of cuvettes containing 1.0 mL pH 8 phosphate buffer/BSA, 100 microL FITC-Anti-Id, and incrementally increasing amounts of E. histolytica antigen, followed by 150 microL RITC-Id is prepared. Fluorescence is measured as described above. Relief from quenching with increasing amounts of E. histolytica is observed forming the basis of the assay.

Although the foregoing invention has been described in some detail by way of illustration and example for purposes of clarity of understanding, it will be obvious that certain changes and modifications may be practiced within the scope of the appended claims.

What is claimed is:

1. A competitive immunoassay for determining the existence of a Dirofilaria immitis infection by analyzing a sample fluid comprising the following steps:
   (a) combining a portion of the sample fluid with an idiotypic antibody to a Dirofilaria immitis antigen and with an antiidiotypic monoclonal antibody to the idotypic antibody, at least one of the two types of antibodies being a labeled antibody, the antiidiotypic monoclonal antibody exhibiting structural congruence with at least one epitope of the antigen, said combining to form an assay mixture in which there is competition between the antigen and the antidiotypic monoclonal antibody for binding to the idiotypic antibody, whereby antiidiotypic-idiotypic antibody pairs are able to form in competition with the formation of antigen-idiotypic antibody pairs in said assay mixture,
   (b) detecting the extent of bound labeled antibody disposed within the antiidiotypic-idiotypic antibody pairs formed as a result of said assay mixture, and
   (c) determining the presence of the antigen in the sample fluid by comparing the extent of bound labeled antibody detected in step (b) with a standard reference derived from a set of antigen standards treated in accordance with steps (a) and (b) wherein the antigen standards are substituted for the sample fluid.

2. A competitive immunoassay according to claim 1 wherein the detecting of the extent of bound labeled antibody disposed within the antiidiotypic-idiotypic antibody pairs follows a physical separation of the antiidiotypic-idiotypic antibody pairs from unbound antibody.

3. A competitive immunoassay according to claim 1 wherein the label has a modulatable signal and the detecting of the extent of bound labeled antibody disposed within the antiidiotypic-idiotypic antibody pairs is by a homogeneous modulation of the label's signal.

4. A competitive immunoassay according to claim 1 wherein the label is an enzyme.

5. A competitive immunoassay according to claim 1 wherein the label is chosen from the group of commonly used labels which includes fluorophores, radionuclides, chemiluminigenic compounds, latex beads, enzyme cofactors and enzyme inhibitors.

6. A competitive immunoassay according to claim 1 wherein the combining of the portion of the sample fluid with the idiotypic antibodies and the antiidiotypic monoclonal antibodies is simultaneous.

7. A competitive immunoassay according to claim 1 wherein the combining of the portion of the sample fluid with the idiotypic antibodies and the antiidiotypic monoclonal antibodies is sequential with the idiotypic antibodies combined firstly and the antiidiotypic monoclonal antibodies combined secondly.

8. A heterogenous competitive immunoassay for determiing the existence of a Dirofilaria immitis infection by analyzing a sample fluid the following steps:
   (a) combining a portion of the sample fluid with an idiotypic antibody to a Dirofilaria immitis antigen and with an antiidiotypic monoclonal antibody to the idiotypic antibody, one of the two types of antibodies being a labeled antibody, the unlabeled antibody being attached to a solid-phase carrier, the antiidiotypic monoclonal antibody exhibiting structural congruence with at least one epitope of the antigen,
      said combining to form an assay mixture having a fluid phase and a solid phase and in which there is competition between the antigen and the antiidiotypic monoclonal antibody for binding to the idiotypic antibody,
      whereby antiidiotypic-idiotypic antibody pairs are able to form in competition with the formation of antigen-idiotypic antibody pairs is said assay mixture,
   (b) subsequently separating the solid-phase carrier from the fluid phase of the assay mixture, the solid-phase carrier carrying its attached antibody and the antigen and antibody which was bound to the attached antibody during step (a),
   (c) subsequently detecting the extend of bound labeled antibody disposed within the antiidiotypic-idiotypic antibody pairs attached and bound to the solid-phase carrier and separated from the assay mixture, and
   (d) determining the presence of the antigen in the sample fluid by comparing the extent of bound labeled antibody detected in step (c) with a standard reference derived from a set of antigen standards treated in accordance with steps (a), (b), and (c) wherein the antigen standards are substituted for the sample fluid.

9. A heterogenous competitive immunoassay as in claim 8 wherein the detecting of the extent of bound labeled antibody disposed within the antiidiotypic-idiotypic antibody pairs attached and bound to the solid-phase carrier and separated from the assay mixture is accomplished by measuring the label bound to the separated solid-phase carrier.

10. A heterogenous competitive immunoassay as in claim 8 wherein the detecting of the extent of bound labeled antibody disposed within the antiidiotypic-idiotypic antibody pairs attached and bound to the solid-phase carrier and separated from the assay mixture is accomplished by measuring the label remaining in the separated fluid phase.

11. A heterogenous competitive immunoassay according to claim 8 wherein the combining of the portion of the sample fluid with the idiotypic antibodies and the antiidiotypic monoclonal antibodies is simultaneous.

12. A heterogenous competitive immunoassay according to claim 8 wherein the combining of the portion of the sample fluid with the idiotypic antibodies and the antiidiotypic monoclonal antibodies is sequential with the idiotypic antibodies combined firstly and the antiidiotypic monoclonal antibodies combined secondly.

13. A heterogenous competitive immunoassay according to claim 8 wherein the label is chosen from the group of commonly used labels which includes enzymes, fluorophores, chemiluminigenic compounds, latex beads, radionuclides, enzyme cofactors, and enzyme inhibitors.

14. A homogeneous competitive immunoassay for determining the existence of a Dirofilaria immitis infection by analyzing a sample fluid comprising the following steps:
   (a) combining a portion of the sample fluid with an idiotypic antibody to a Dirafilaria immitis antigen and with an antiidioty monclonal antibody to the idiotypic antibody, at least one of the two types of antibodies being covalently coupled to a modulatable lable, the antiidiotypic monoclonal antibody exhibiting structural congruence with at least one epitope of the antigen,
      said combining to form an assay mixture in which there is competition between the antigen and the antiidiotypic monoclonal antibody for binding to the idiotypic antibody,
      whereby antiidiotypic-idiotypic antibody pairs are able to form in competition with the formation of antigen-idiotypic antibody pairs in said assay mixture,
   (b) subsequently detecting the extend of bound labeled antibody disposed within the antiidiotypic-idiotypic antibody pairs by measuring the modulation of the label, and
   (c) determining the presence of the antigen in the sample fluid by comparing the extent of bound labeled antibody detected in step (b) with a standard reference derived from a set of antigen standards treated in accordance with steps (a), and (b) wherein the antigen standards are substituted for the sample fluid.

15. A homogeneous competitive immunoassay according to claim 14 wherein the modulatable label is selected from the group of commonly used labels which include enzymes, fluorophores, chemiluminigenic compounds, enzyme cofactors, and enzyme inhibitors.

16. An immunoassay for determining the existence of a Dirofilaria immitis infection by analyzing a sample fluid to detect the presence of an antibody comprising the following steps:
   (a) combining a portion of the sample fluid with an antiidiotypic monoclonal antibody to the anti-Dirofilaria-immitis antibody, the antiidiotypic monoclonal antibody exhibiting structural congruence with at least one epitope of the Dirofilaria immitis antigen to which the antibody is capable of binding, the antiidiotypic monoclonal antibody attached to a solid-phase carrier,
      said combining to form an assay mixture having a fluid phase and a solid phase and in which the antibody is allowed to bind to antiidiotypic monoclonal antibody to form antibody-antiidiotypic antibody pairs,
   (b) adding a labeled antiglobin to the assay mixture for enabling the antiglobin to bind to the antibody and to the antibody-antiidiotypic antibody pairs attached to the solid-phase carrier to form antiglobin-antibody-antiidiotypic antibody complexes, and
   (c) subsequently separating the solid-phase carrier from the fluid phase of the assay mixture, the solid-phase carrier carrying the antiglobin-antibody-antiidiotypic antibody complexes,
   (d) subsequently detecting the extent of bound labeled antiglobin disposed within the antiglobin-antibody-antiidiotypic antibody complexes, attached and bound to the solid-phase carrier and separated from the assay mixture, and (e) determining the presence of the antibody in the sample fluid by comparing the extend of bound labeled antibody detected in step (d) with a standard reference derived from a set of antigen standards treated in accordance with steps (a), (b), (c), and (d) wherein the antigen standards are substituted for the sample fluid.

17. A method according to claim 16 wherein the label is chosen from the group of commonly used labels including enzymes, fluorophores, chemiluminigenic compounds, enzyme cofactors, enzyme inhibitors, and latex particles.

18. An antiidiotypic monoclonal antibody reagent for assaying an antigen from Dirofilaria immitis comprising,
   (a) a purified antiidiotypic monoclonal antibody and
   (b) a label attached to said purified antiidiotypic monoclonal antibody,
      said purified antiidiotypic monoclonal antibody exhibiting a structural congruence with at least one epitope of a Dirofilaria immitis antigen,
      said attached label having a modulatable signal that is detectable when disposed within the antiidiotypic-idiotype pairs for assaying the antigen.

19. An antiidiotypic monoclonal antibody reagent according to claim 18 wherein the label is selected from the group of commonly used modulatable labels which includes enzymes, fluorophores, chemiluminigenic compounds, enzyme cofactors, and enzyme inhibitors.

20. An antiidiotypic monoclonal antibody reagent for assaying an antigen from Dirofilaria immitis or an idiotypic antibody to said antigen comprising:
   (a) a purified antiidiotypic monoclonal antibody and
   (b) a solid-phase carrier attached to said purified antiidiotypic monoclonal antibody,
      said purified antiidiotypic monoclonal antibody exhibiting a structural congruence with at least one epitope of a Dirofilaria immitis antigen,
      said attached solid-phase carrier enabling the antiidiotypic monoclonal antibody to be physically separated from the fluid mixture.

21. An antiidiotypic monoclonal antibody reagent according to claim 20 further comprising:
   (c) a label attached to said purified antiidiotypic monoclonal antibody,
      said attached label detectable when disposed within the antiidiotypic-idiotype pairs for assaying the antigen.

22. An antiidiotypic monoclonal antibody reagent according to claim 21 wherein the label is chosen from the group of commonly used labels used in heterogeneous immunoassays which includes enzymes, fluorophores, chemiluminigenic compounds, radionuclides, enzyme cofactors, and enzyme inhibitors.

* * * * *